United States Patent [19]
Matsuura et al.

[11] Patent Number: 5,900,359
[45] Date of Patent: May 4, 1999

[54] METHOD FOR DETERMINATION OF OXIDIZED LIPOPROTEINS AND USE THEREOF

[75] Inventors: Eiji Matsuura; Tomoyoshi Katahira, both of Choshi; Takao Koike, Sapporo, all of Japan

[73] Assignee: Yamasa Corporation, Chiba-Ken, Japan

[21] Appl. No.: 08/624,366

[22] PCT Filed: Sep. 28, 1994

[86] PCT No.: PCT/JP94/01594

§ 371 Date: Mar. 28, 1996

§ 102(e) Date: Mar. 28, 1996

[87] PCT Pub. No.: WO95/09363

PCT Pub. Date: Apr. 6, 1995

[30] Foreign Application Priority Data

Sep. 29, 1993 [JP] Japan ................................. 5-265606
Dec. 24, 1993 [JP] Japan ................................. 5-347404

[51] Int. Cl.[6] .................................................. G01N 33/53
[52] U.S. Cl. .................... 435/7.1; 435/7.92; 435/7.93; 435/7.94; 435/960; 435/971; 435/975; 436/506; 436/518; 436/501; 436/507; 436/528; 436/532; 436/540; 436/808; 436/811; 436/536; 530/389.1; 530/389.3; 530/380; 530/359; 530/387.1

[58] Field of Search ............................ 436/518, 501, 436/506, 507, 528, 532, 538, 540, 808, 811, 536; 530/389.1, 389.3, 380, 359, 387.1; 435/7.1, 7.92, 7.93, 7.94, 960, 971, 975

[56] References Cited

U.S. PATENT DOCUMENTS 4,877,746 10/1989 Jansson et al. .
5,472,883 12/1995 Matsuura et al. .

OTHER PUBLICATIONS

Clark et al. 1987 Enzyme–Immunoassay, ed., by Edward T. Maggio CRC Press, Inc. Flonor, Chapter 8 pp. 167–178.
Hashimoto et al. (1992) J. Immunol. 149 (3), 1063–8.
McNally et al (1993) Nov. 15., vol. 72, 275–286.

*Primary Examiner*—Paula K. Hutzell
*Assistant Examiner*—Khalid Masood
*Attorney, Agent, or Firm*—Wenderoth, Lind & Ponack, L.L.P.

[57] ABSTRACT

Use of an anti-cardiolipin antibody, anti-lipoprotein antibody or anti-β2-glycoprotein I antibody together with an immobilized antibody thereof enables to accurately assay for a complex of β2-glycoprotein I and an oxidized lipoprotein in a blood sample, according to a sandwich immunoassay. Thus, the oxidized lipoprotein in blood can be detected, whereby diagnosis of arteriosclerotic disease is enabled.

10 Claims, 8 Drawing Sheets

Ox LDL

NATIVE LDL

METHOD FOR DETERMINATION OF OXIDIZED LIPOPROTEINS AND USE THEREOF

This application is a 371 of PCT/JP94/01594 filed Sep. 28, 1994.

BACKGROUND OF THE INVENTION

1. Field of the Invention

The present invention relates to a method for the immunological determination of oxidized lipoproteins utilizing the specific binding of oxidized lipoproteins to β2-glycoprotein I (β2-GPI), and to use thereof.

2. Description of Related Art

In general, lipids are sparingly soluble in water and hence are transported in vivo from one tissue to another in the form of lipoproteins, wherein triglycerides and cholesterol esters as non-polar lipids form a core which is covered with phospholipids and proteins. Depending on hydration density, lipoproteins are classified into four groups: chylomicron (up to 0.950 g/ml), very low density lipoprotein (VLDL, in the range of 0.950 to 1.006 g/ml), low density lipoprotein (LDL, in the range of 1.006 to 1.063 g/ml) and high density lipoprotein (HDL, in the range of 1.063 to 1.210 g/ml). The protein components in these lipoproteins are called "apolipoproteins".

Lipoproteins are deeply associated with the development and progress of arteriosclerosis as well as in vivo transport of lipids. One of the risk-factors for arteriosclerotic disease such as coronary arterioclerosis and cerebral arteriosclerosis is hyperholesterolemia wherein lipoproteins level (especially LDL level) in blood are increased. It is considered that in these diseases, LDL would take part in advancing arteriosclerosis, whereas HDL would have the opposite action to suppress arteriosclerosis.

Recent studies suggest that oxidized lipoproteins might accelerate the development of arteriosclerosis. That is, it is reported that at the initial stage of arteriosclerosis, an endothelial macrophage specifically phagocytoses an oxidized LDL abundant in cholesterol through a receptor to convert the oxidized LDL into foam cells. In contrast, a non-oxidized LDL is not phagocytosed by macrophage. This is also supported by the fact that oxidized LDL is observed in an immunological tissue staining utilizing antibodies to oxidized LDL to be widely distributed at the focal site of arteriosclerosis. It is also revealed that HDL possesses an activity of stimulating the release of cholesterol from foam cells, whereas this activity is seriously reduced in oxidized HDL.

As described above, it has been suggested that the development of arteriosclerotic diseases might be closely associated with oxidized lipoproteins. Accordingly, there is a possibility that assaying specifically for the oxidized lipoproteins could be of some assistance to analysis of the development mechanism of arteriosclerosis and to diagnosis for arteriosclerotic disease.

It is known that the oxidized lipoproteins are assayed by RIA or EIA using antibodies obtained by immunization of oxidized lipoproteins, as reported in Biochimica et Biophysica Acta, 963, 208–214 (1988), Proc. Natl. Acad. Sci. USA, 86, 1372–1376 (1989) and Clinica Chimica Acta, 218, 97–103 (1993).

SUMMARY OF THE INVENTION

The inventors have made detailed analysis on the form of oxidized lipoproteins present in blood. As a result, it has been found that β2-GPI circulating in blood binds to oxidized lipoproteins at the oxidized site thereof. Further, it has been suggested that a complex of β2-GPI and an oxidized lipoprotein would have an epitope similar to one present only in a complex of β2-GPI and a phospholipids, because anti-cardiolipin antibodies derived from patients with antiphospholipid antibody syndrome react with the complex of β2-GPI and an oxidized lipoprotein. The present invention has thus been accomplished.

That is, the present invention relates to a method for determining the complex of β2-GPI and an oxidized lipoprotein (β2-GPI-oxidized lipoprotein complex) by a sandwich assay, using at least two reagents, a solid phase reagent selected from Group A below and an antibody reagent selected from Group B below (Method 1 of the present invention), and to a kit or use in the method (Kit 1 of the present invention):

Group A
 (1) an immobilized anti-cardiolipin antibody
 (2) an immobilized anti-lipoprotein antibody or an immobilized anti-apolipoprotein antibody
 (3) an immobilized anti-β2-GPI antibody Group B
 (1) an anti-cardiolipin antibody
 (2) an anti-lipoprotein antibody or an anti-apolipoprotein antibody
 (3) an anti-β2-GPI antibody.

The present invention further relates to a method for the determination of the β2-GPI-oxidized lipoprotein complex by a competitive immunoassay, using a solid phase reagent selected from Group C below and an anti-cardiolipin antibody as an antibody reagent (Method 2 of the present invention), and to a kit for use in the method (Kit 2 of the present invention).

Group C
 (1) an immobilized cardiolipin-β2-GPI complex
 (2) a β2-GPI immobilized on a specific carrier.

The present invention further relates to use of the foregoing methods and kits for use in diagnosis for arteriosclerotic disease.

DESCRIPTION OF THE PREFERRED EMBODIMENTS

Figure 1:
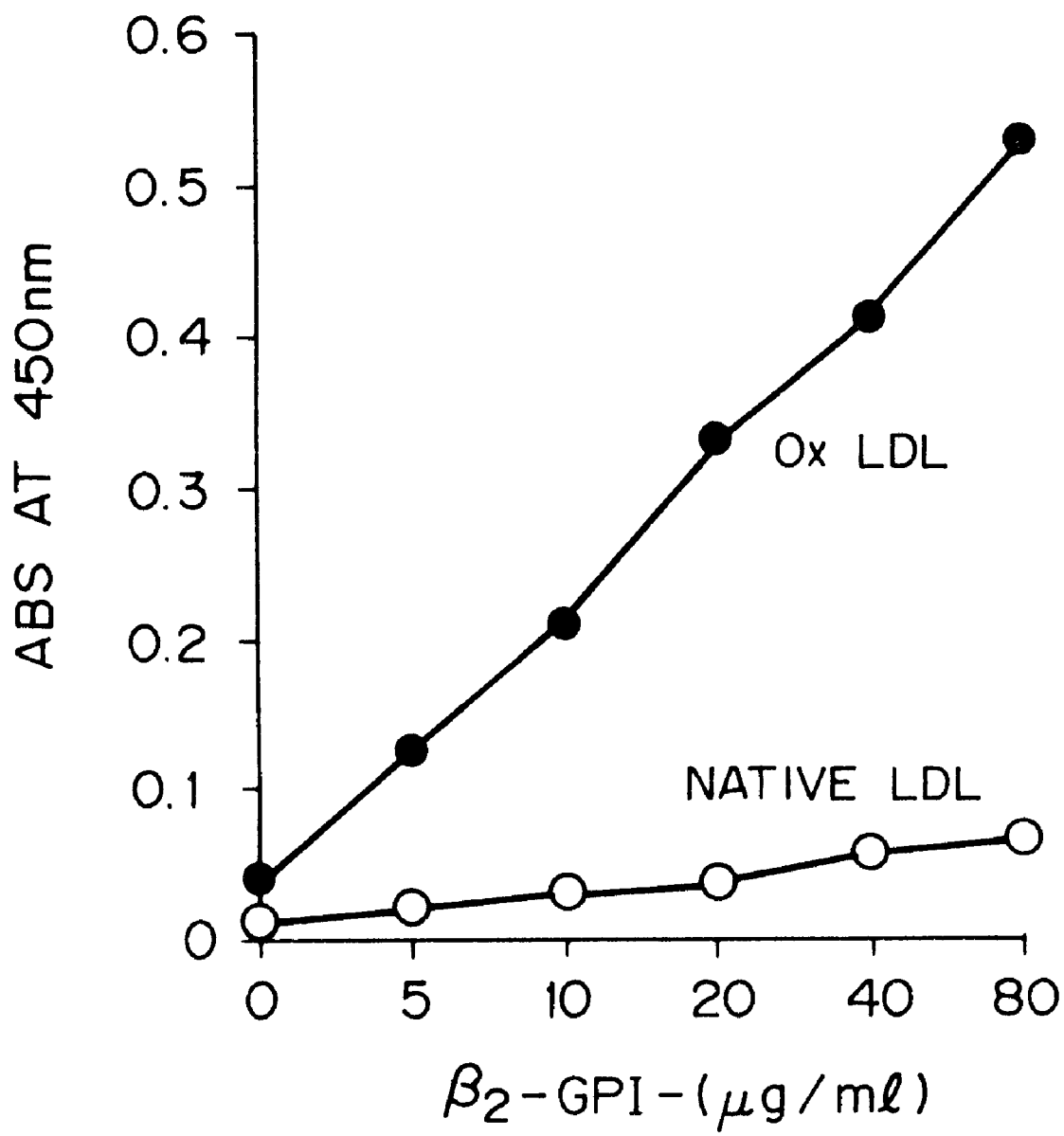
FIG. 1 shows the specific binding of β2-GPI to an oxidized LDL.

The technical terms used throughout the present specification are defined as follows.

β2-GPI

β2-GPI is a known serum protein that has its noticeable role for an endogenous coagulation system.

In the present invention, any β2-GPI may be employed as far as it is derived from mammal. The β2-GPI may also be modified so as to delete of its sugar chain partially or wholly.

Anti-β2-GPI antibody

Anti-β2-GPI is an antibody capable of binding to β2-GPI. Particularly preferred is an antibody that does not recognize a site on β2-GPI to which an oxidized lipoprotein bind.

Anti-cardiolipin antibody

Anti-cardiolipin antibody is an antibody capable of reacting with the complex of phospholipid and β2-GPI, which is observed in serum from patients with autoimmune disease such as anti-phospholipid antibody syndrome.

Anti-lipoprotein antibody

Anti-lipoprotein antibody is an antibody capable of binding to a lipoprotein. Particularly preferred is an antibody that does not recognize a β2-GPI-binding site on an oxidized lipoprotein.

Anti-apolipoprotein antibody

Anti-apolipoprotein antibody is an antibody capable of binding to an apolipoprotein component in a lipoprotein. Particularly preferred is an antibody that does not recognize a β2-GPI-binding site on an oxidized lipoprotein.

β2-GPI immobilized on a specific carrier

The β2-GPI is immobilized on a synthetic resin as the carrier having a polar group such as hydroxy, carbonyl and carboxyl introduced on the surface by a physical or chemical means.

The sample used in the present invention has no particular restriction but may be any biological sample so long as the sample is suspected of containing oxidized lipoproteins. Specifically, the sample may be whole blood or fraction thereof such as serum and plasma. It is important that the sample containing oxidized lipoproteins is pretreated by adding β2-GPI thereto to form the β2-GPI-oxidized lipoprotein complex in the sample. The pretreatment of the sample may be omitted, when a sample such as a serum originally contains β2-GPI sufficiently to form the β2-GPI-oxidized lipoprotein complex in the sample without the addition of β2-GPI. The pretreatment may also be conducted at the same time when the immunological reaction is carried out in accordance with the method of the present invention.

(1) Method of the invention

As described above, Method 1 of the present invention is directed to a method for determining an oxidized lipoprotein in a sample by a sandwich assay which comprises assaying for the β2-GPI-oxidized lipoprotein complex, using at least two reagents, a solid phase reagent selected from Group A below and an antibody reagent selected from Group B below:

Group A
  (1) an immobilized anti-cardiolipin antibody
  (2) an immobilized anti-lipoprotein antibody or an immobilized anti-apolipoprotein antibody
  (3) an immobilized anti-β2-GPI antibody Group B
  (1) an anti-cardiolipin antibody
  (2) an anti-lipoprotein antibody or an anti-apolipoprotein antibody
  (3) an anti-β2-GPI antibody.

The reagents in Groups A and B may be used in any combination thereof, without any particular restriction, as long as the reagents function so as to determine an oxidized lipoprotein in the sample. Preferred examples of the combination of a reagent in Group A with that in Group B are as follows.

Combination 1
  Group A: an immobilized anti-cardiolipin antibody
  Group B: an anti-lipoprotein antibody or an
    anti-apolipoprotein antibody,
    and/or an anti-β2-GPI antibody Combination 2
  Group A: an immobilized anti-lipoprotein
    antibody or an immobilized anti-apolipoprotein antibody
  Group B: an anti-cardiolipin antibody and/or
    an anti-β2-GPI antibody Combination 3
  Group A: an immobilized anti-β2-GPI antibody
  Group B: an anti-cardiolipin antibody and/or
    an anti-lipoprotein antibody or an
    anti-apolipoprotein antibody Combination 4
  Group A: an immobilized anti-cardiolipin antibody
  Group B: an anti-cardiolipin antibody.

More preferred examples of the combination of the reagents are given below.

Combination 5
  Group A: an immobilized anti-cardiolipin antibody
  Group B: an anti-lipoprotein antibody or an
    anti-apolipoprotein antibody Combination 6
  Group A: an immobilized anti-lipoprotein
    antibody or an immobilized anti-apolipoprotein antibody
  Group B: an anti-cardiolipin antibody and/or
    an anti-β2-GPI antibody Combination 7
  Group A: an immobilized anti-β2-GPI antibody
  Group B: an anti-lipoprotein antibody or an
    anti-apolipoprotein antibody Antibodies which can be employed in preparing the reagents of Groups A and B may be prepared by well-known conventional methods.

For example, the anti-cardiolipin antibody may be serum from patients with anti-phospholipid antibody syndrome, an antibody fraction isolated and purified from the serum, or a monoclonal antibody obtained by cell fusion between myeloma cells and spleen cells of F1 mouse from NZW mouse and BXSB mouse.

Some of the anti-lipoprotein antibody, anti-apolipoprotein antibody and anti-β2-GPI antibody are commercially available; in such a case, these anti-bodies available on the market may be employed for the present invention. Furthermore, the antibodies may also be prepared in a conventional manner using known serum proteins as antigens. The thus prepared antibodies may be used in the present invention. These antibodies used are not particularly limited, and may be a polyclonal antibody, a monoclonal antibody or its active fragment (F(ab')$_2$, Fab', and the like).

Preferably, the serum proteins used as antigens in preparing the antibodies should be derived from mammal. The proteins may be isolated and purified from serum, or prepared by a recombinant DNA technique.

A carrier which is employed to prepare the solid phase reagents in Group A as described above may be any conventional carrier. Typical examples of the carrier include a synthetic organic high molecular compound such as polyvinyl chloride, polystyrene, styrene-divinylbenzene copolymer, styrene-maleic anhydride copolymer, nylon, polyvinyl alcohol, polyacrylamide, polyacrylonitrile, polypropylene and polymethylene methacrylate; a polysaccharide such as a dextran derivative (Sephadex, etc.), an agarose gel (Sepharose, Biogel, etc.), a cellulose (paper disk, filter paper, etc.); and an inorganic high molecular compound such as glass, silica gel and silicone. These carriers may be modified by introducing thereon functional groups such as amino, carboxyl, carbonyl, hydroxy and sulfhydryl group. Particularly preferred examples of the carrier are polystyrene and polyvinyl chloride.

The carrier may take any shape such as a flat plate (microtiter plate, disk, etc.), particles (beads, etc.), a tube (a testing tube, etc.), fibers, membrane, fine particles (latex particles, etc.), capsules and vesicles. The shape of the carrier may be appropriately chosen depending on the an assay method used.

The solid phase reagents in Group A as described above may be prepared by immobilizing a desired antibody on the carrier. The immobilization of the antibody on the surface of the carrier may be effected by conventional methods such as physical adsorption, ionic binding, covalent binding, and entrapping, as disclosed in Ichiro Chihata, "KOTEIKA KOUSO (Immobilized Enzyme)", published Mar. 20, 1975, Kodansha Publishing Inc. Particularly, physical adsorption is advantageous because of its simplicity. The antibody may be immobilized directly on the surface of the carrier. Alternatively, the antibody may be indirectly immobilized through other substance (a spacer, etc.) on the surface of the carrier.

The solid phase reagent thus obtained may also be subjected to a blocking treatment with a conventional blocking agent such as gelatin and BSA, in order to avoid occurrence of undesirable non-specific binding.

The antibody reagent in Group B as described above may also be labeled with a label conventionally employed for an immunoassay. Examples of such a label include a radioisotope ($^{32}$P, $^{3}$H, $^{14}$C, $^{125}$I, etc.); an enzyme (β-galactosidase, peroxidase, alkaline phosphatase, glucose-6-phosphate dehydrogenase, catalase, glucose oxidase, lactate oxidase, alcohol oxidase, monoamine oxidase, etc.); a coenzyme or a prosthetic group (FAD, FMN, ATP, biotin, hem, etc.); a fluorescein derivative (fluorescein isothiocyanate, fluorescein thioflubamyl etc.); a fluorescent dye such as a rhodamine derivative (tetramethylrhodamine B isothiocyanate, etc.), umbelliferone, 1-anilino-8-naphthalenesulfonic acid, and the like; a luminol derivative (luminol, isoluminol, N-(6-aminohexyl)-N-ethylisoluminol, etc.).

Labeling of the antibody with the label may be carried out by choosing an appropriate method from conventional methods as described in textbooks (e.g., "ZOKU SEIKAGAKU JIKKEN KOZA, 5. MEN-EKI SEIKAGAKU KENKYUHO (Supplemental to Lecture Series on Biochemical Experiment, 5. Study on Immunological Biochemistry)", pages 102–112, 1986, published by Tokyo Kagaku Dojin Publishing Inc.).

Conventional sandwich immunoassay procedures may be used, in order to determine whether the oxidized lipoprotein is present in a sample using the solid phase reagent and the antibody reagent. That is, the oxidized lipoprotein in a sample can be assayed either by reacting a sample with the solid phase reagent, and further performing B/F separation, if necessary and desired, then reacting with the antibody reagent (a so-called two-step method), or by reacting a sample with the solid phase reagent together with the antibody reagent (a so-called one-step method). In any case, after the reaction has been completed, the oxidized lipoprotein in the sample can be detected or quantitatively determined in a conventional manner.

Method 2 of the present invention is directed to a method for determining the β2-GPI-oxidized lipoprotein complex in a sample by a competitive immunoassay, using a solid phase reagent selected from Group C below and an anti-cardiolipin antibody as the antibody reagent:

Group C (1) an immobilized cardiolipin-β2-GPI complex
(2) a β2-GPI immobilized on a specific carrier.

Examples of the anti-cardiolipin antibody used as the antibody reagent are the same as those exemplified for Group B as described above.

In the solid phase reagents of Group C as described above, the immobilized cardiolipin-β2-GPI complex is obtained by immobilizing a cardiolipin on a carrier, which is the same as the carrier used for immobilizing the antibody, in a conventional manner, then reacting further with β2-GPI.

The β2-GPI immobilized on the specific carrier may be obtained in the same way as in the immobilized antibody reagent as described above, except that β2-GPI is immobilized on a specific carrier. As defined hereinabove, the specific carrier may be a synthetic resin having a polar group such as hydroxy, carbonyl and carboxyl introduced on the surface by an appropriate physical and/or chemical treatment (e.g., exposure to radiation or ozone treatment). Specific examples of the carrier are EB plate (Labo Systems Inc.), H type plate, C type plate (Sumitomo Bakelite Co.), or other synthetic resins having a polar group such as "MAX-ISORP" plate (Nunc Inc.).

Conventional competitive immunoassay procedures may be used, in order to determine whether the oxidized lipoprotein is present in a sample, using the solid phase reagent and the antibody reagent as described above. That is, the β2-GPI-oxidized lipoprotein complex in the sample and the solid phase reagent are reacted competitively with the antibody reagent; after the reaction has been completed, the oxidized lipoprotein in the sample is detected or quantitatively determined in a conventional manner.

The details of immunoassay such as a sandwich assay and a competitive immunoassay are described in the following publications:

(1) Hiroshi Irie, "ZOKU RADIOIMMUNOASSAY (Supplemental to Radioimmunoassay)", published May 1, 1979 by Kodansha Publishing Inc.;
(2) Eiji Ishikawa et al., "KOUSO MENEKI SOKUTEIHO (Enzyme Immunoassay)" (second edition), published Dec. 15, 1982 by Igaku Shoin Publishing Inc.;
(3) RINSHO BYORI (Clinical Pathology), extra issue, special edition No. 53 "Immunoassay for clinical test its technique and application", 1983, published by Rinsho Byori Kanko Kai;
(4) "Dictionary of Biotechnology", published Oct. 9, 1986 by CMC Co.;
(5) Methods in ENZYMOLOGY, Vol. 70, Immunochemical techniques (Part A);
(6) Methods in ENZYMOLOGY, Vol. 73, Immunochemical techniques (Part B);

(7) Methods in ENZYMOLOGY, Vol. 74, Immunochemical techniques (Part C);
(8) Methods in ENZYMOLOGY, Vol. 84, Immunochemical techniques (Part D: Selected Immunoassay);
(9) Methods in ENZYMOLOGY, Vol. 92, Immunochemical techniques (Part E: Monoclonal Antibodies and General Immunoassay Methods).

All the above publications (5) through (9) were published by Academic Press.

(2) Kit of the Present invention

In the kit for assay of the present invention, Kit 1 and Kit 2 are used for the Methods 1 and 2 in accordance with the present invention, respectively.

That is, Kit 1 comprises as constituent reagents at least two reagents, a solid phase reagent selected from Group A below and an antibody reagent selected from Group B below:

Group A
(1) an immobilized anti-cardiolipin antibody
(2) an immobilized anti-lipoprotein antibody or an immobilized anti-apolipoprotein antibody
(3) an immobilized anti-$\beta$2-GPI antibody Group B
(1) an anti-cardiolipin antibody
(2) an anti-lipoprotein antibody or an anti-apolipoprotein antibody
(3) an anti-$\beta$2-GPI antibody.

Kit 2 comprises as constituent reagents a solid phase reagent selected from Group C below and an anti-cardiolipin antibody as the antibody reagent.

Group C
(1) an immobilized cardiolipin-$\beta$2-GPI complex
(2) a $\beta$2-GPI immobilized on a specific carrier.

The reagents of Groups A through C may be prepared by the methods described hereinabove. In addition to the reagents of Groups A to C, the kit of the present invention may further include, if necessary, additional reagents suitable for an assay method used. Those additional reagents may be appropriately selected from a color-forming reagent, a reagent for terminating the reaction, a standard antigen reagent, a reagent for pretreating the sample, and the like.

Hereinafter the present invention will be described more specifically by referring to the following Examples.

(1) Antibodies used in Examples

1) Antibody SLE-1

Antibody SLE-1 is a serum which is positive to an anti-cardiolipin (aCL) antibody derived from patients with anti-phospholipid antibody syndrome, and possesses a binding ability to the complex of cardiolipin and $\beta$2-GPI.

2) Antibodies WB-CAL-1 and WB-CAL-3

Antibodies WB-CAL-1 and WB-CAL-3 are monoclonal aCL antibodies, which have been obtained from a hybridoma produced by cell fusion between aCL antibody-producing cells derived from NZW×BXSB F1 (W/B F1) mouse and myeloma cells (The Journal of Immunology, 149, 1063–1068 (1992)). The antibodies are capable of binding to the complex of cardiolipin and $\beta$2-GPI.

3) Antibody Cof-22

Antibody Cof-22 is a monoclonal anti-$\beta$2-GPI antibody obtained from a hybridoma which has been produced by cell fusion between myeloma cells and spleen cells from BALB/c mouse immunized with human $\beta$2-GPI. The antibody is capable of binding to $\beta$2-GPI (WO 92/19755) but does not recognize a site on the $\beta$2-GPI, to which an oxidized lipoprotein binds.

4) Antibodies 9F5-3 and 10E3-3

Antibodies 9F5-3 and 10E3-3 are monoclonal anti-LDL antibodies obtained from hybridomas which have been produced by cell fusion between myeloma cells and spleen cells from BALB/c mouse immunized with oxidized LDL. The antibodies are capable of binding both to an oxidized LDL and non-oxidized LDL but does not recognize a $\beta$2-GPI-binding site on the oxidized LDL, as shown on FIG. 3.

These antibodies may be readily obtained by known methods, as described in, for example, J. Biol. Chem., 269, 15274–15279 (1994); Science, 241, 215–218 (1988); Am. J. Pathol., 135, 815–825 (1989); and Biochim. Biophys. Acta, 963, 208–214 (1988).

5) Antibodies 1D2 and 5G6

Antibodies 1D2 and 5G6 are monoclonal anti-apo B protein antibodies obtained from hybridomas which have been produced by cell fusion between myeloma cells and spleen cells from BALB/c mouse immunized with human purified apo B protein (Medix Biotech Inc., Foster, Calif.). The antibodies are capable of binding to apo B protein but do not recognize a $\beta$2-GPI-binding site on the oxidized LDL.

These antibodies are commercially available from Chemicon Inc., and the like, and those antibodies may be employed for the kit of the present invention.

6) Antibody H1

Antibody H1 is a monoclonal anti-HDL antibody. The antibody is capable of binding both to an oxidized HDL and non-oxidized HDL but does not recognize a $\beta$2-GPI-binding site on the oxidized HDL.

The antibody may be readily obtained by known methods as explained for the anti-LDL antibody above.

(2) Preparation of oxidized LDL

In 2 ml of PBS containing 5 $\mu$M $CuSO_4$, 600 $\mu$g of human LDL (Organon Teknika Corp., Durham, N.C.) was treated at 37° C. for 24 hours.

(3) Quantitative determination of lipid peroxides present in LDL

First, 0.1 ml of 8.1% SDS, 0.75 ml of 20% acetic acid (pH 3.5) and 0.75 ml of 0.8% thiobarbituric acid were added to 0.4 ml of each sample containing a non-oxidized LDL or oxidized LDL. The mixture was then reacted at 95° C. for an hour. After cooling, 0.5 ml of distilled water and 2.5 ml of mixture of n-butanol and pyridine (15:1) were added to the reaction mixture followed by stirring. The mixture was centrifuged at 3000 rpm for 20 minutes. The organic phase was then collected, and absorbance was measured at 532 nm. For control, tetramethoxypropane was also employed. When the amount of a lipid peroxide is expressed in terms of a malonedialdehyde equivalent, the non-oxidized LDL showed 8.8 nmol/mg, whereas the oxidized LDL showed 50.8 nmol/mg.

EXAMPLE 1

Binding of $\beta$2-GPI to oxidized LDL (FIG. 1)

After 50 $\mu$l of 2 $\mu$g/ml oxidized LDL (OxLDL) or 2 $\mu$g/ml non-oxidized LDL (native LDL) was charged in each well on a polystyrene plate, the wells were incubated at 4° C. for 16 to 24 hours. After washing with 0.05% Tween 20-containing PBS (PBS-Tween), 100 $\mu$l of appropriately diluted $\beta$2-GPI was added to each well followed by incubation at room temperature for an hour. After washing, 100 $\mu$l of peroxidase-labeled anti-$\beta$2-GPI antibody (Antibody Cof-22) was charged in each well and incubated at room temperature for further one hour. After washing, 100 $\mu$l of a 0.3 mM tetramethylbenzidine (TMBZ) solution containing 0.005% hydrogen peroxide was added to each well and incubated at room temperature for 10 minutes. The reaction was then terminated with the addition of 100 μl of 2N sulfuric acid. The absorbance was measured at 450 rnm.

As shown in FIG. 1, the results reveal that β2-GPI binds only to the oxidized LDL.

Figure 2A:
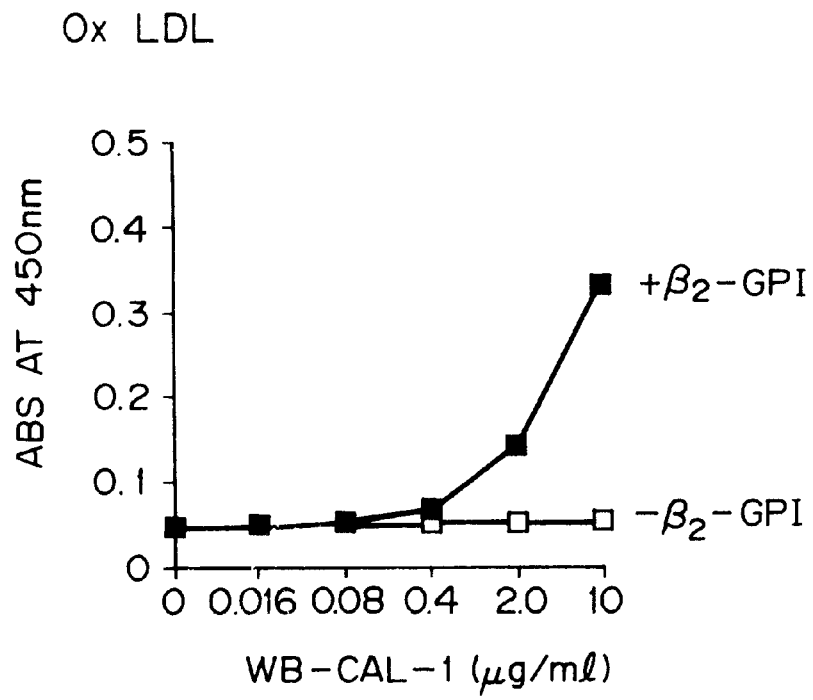
FIG. 2 shows the reactivity of an anti-cardiolipin (aCL) antibody with the β2-GPI-oxidized LDL complex.
Figure 2B:
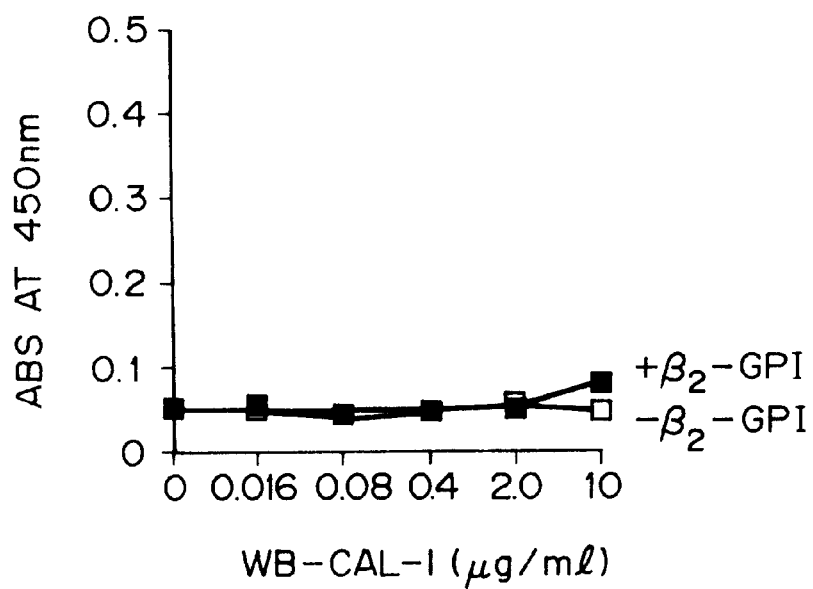
Figure 3A:
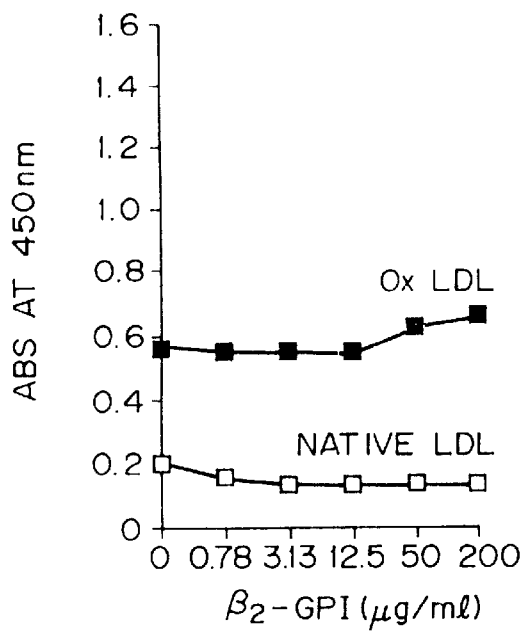
FIG. 3 shows the reactivities of an anti-LDL antibody and an anti-apo B protein antibody.
Figure 3B:
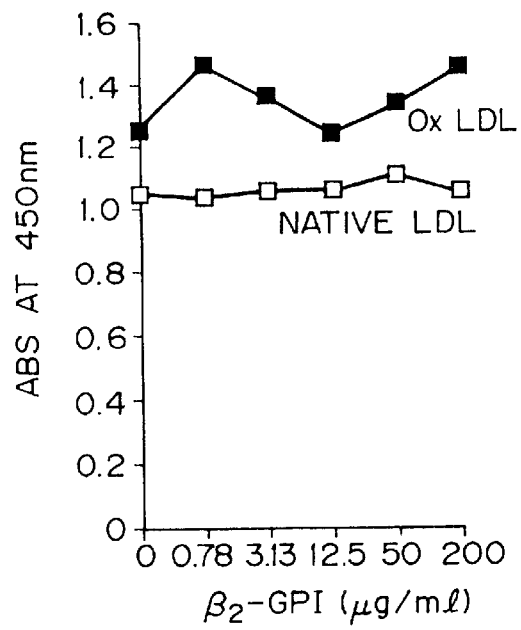
Figure 3C:
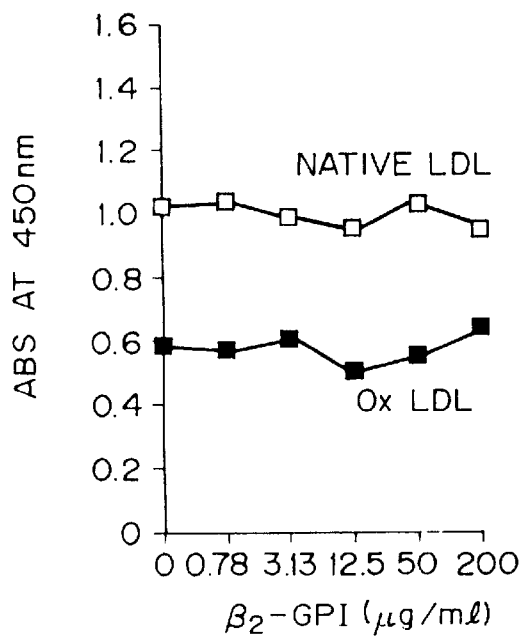
Figure 3D:
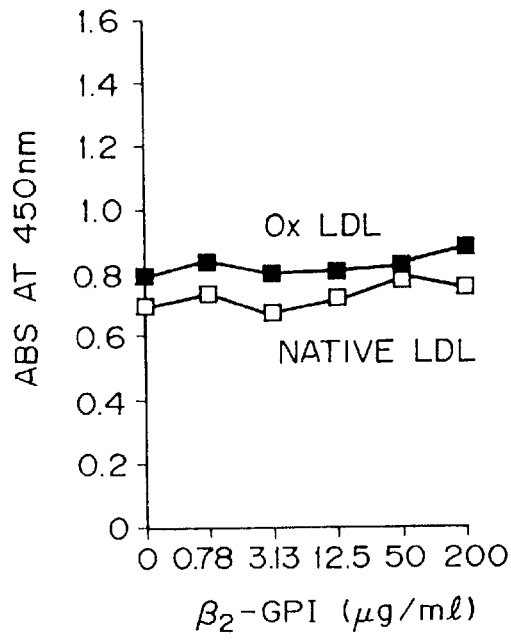

EXAMPLE 2
Reactivity of aCL antibody with the β2-GPI-oxidized LDL complex (FIG. 2).

After 50 μl of 2 μg/ml oxidized LDL or 2 μg/ml non-oxidized LDL was charged in each well on a polystyrene plate, the wells were incubated at 4° C. for 16 to 24 hours. After the wells were then washed with PBS-Tween, appropriately diluted Antibody WB-CAL-1 was reacted at room temperature for an hour in the presence or absence of β2-GPI (100 μg/ml). After washing, 100 μl of peroxidase-labeled anti-mouse IgG antibody was charged in each well and incubated at room temperature for further one hour. After washing, 100 μl of a 0.3 mM TMBZ solution containing 0.005% hydrogen peroxide was added to each well and incubated at room temperature for 10 minutes. The reaction was then terminated with the addition of 100 μl of 2N sulfuric acid. The absorbance was measured at 450 nm.

As shown in FIG. 2, the results reveal that the aCL antibody binds only to the β2-GPI-oxidized LDL complex.

EXAMPLE 3
Reactivity of anti-LDL antibody and anti-apo B protein antibody (FIG. 3)

After 50 μl of 2 μg/ml oxidized LDL or 2 μg/ml non-oxidized LDL was charged in each well on a polyvinyl chloride plate, the wells were incubated at 4° C. for 16 to 24 hours, then washed with PBS. After 200 μl of 3% gelatin solution was added to each well, the wells were incubated for an hour at room temperature. After the gelatin solution was removed, appropriately diluted β2-GPI and a predetermined amount of peroxidase-labeled anti-LDL antibodies (Antibodies 9F5-3 and 10E3-3) or peroxidase-labeled anti-apo B protein antibodies (Antibodies 1D2 and 5G6) were reacted, in total volume of 50 μl, at room temperature for an hour. After washing, 100 μl of a 0.3 mM TMBZ solution containing 0.005% hydrogen peroxide was added to each well, and incubated at room temperature for 10 minutes. The reaction was then terminated with the addition of 50 μl of 2N sulfuric acid. The absorbance was measured at 450 nm.

As shown in FIG. 3, the results reveal that both the anti-LDL antibody and anti-apo B protein antibody do not recognize a β2-GPI-binding site on the oxidized LDL.

Figure 4A:
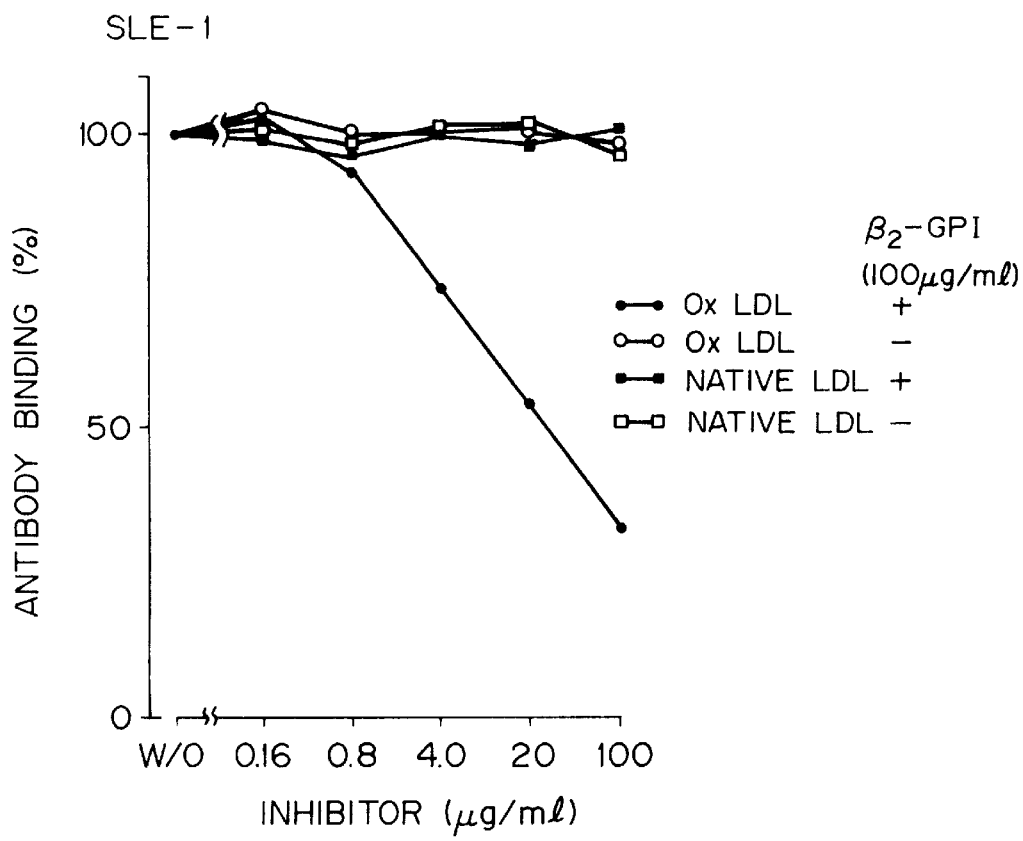
FIG. 4 shows the results of assay for an oxidized LDL by competitive ELISA, using an aCL antibody.
Figure 4B:
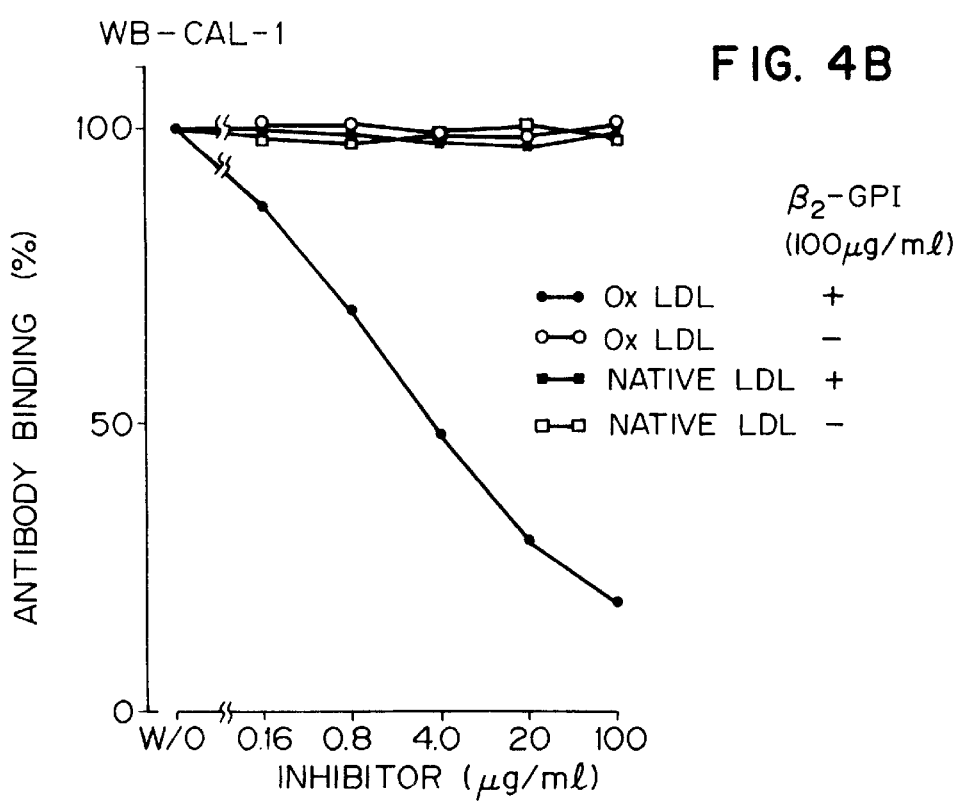

EXAMPLE 4
Assay for oxidized LDL by competitive ELISA (FIG. 4)

After 50 μl of 10 μg/ml β2-GPI was charged in each well on a polystyrene plate wherein a polar group containing an oxygen atom had been introduced on the surface (C type plate, Sumitomo Bakelite Co., Ltd.), the wells were incubated at 4° C. for 16 to 24 hours, then washed with PBS-Tween. Thereafter aCL antibody, i.e., 100-fold-diluted Antibody SLE-1 or 0.5 μg/ml of Antibody WB-CAL-1 was incubated with appropriately diluted oxidized LDL or non-oxidized LDL at room temperature for an hour, in the presence or absence of β2-GPI (100 μg/ml). After washing, 100 μl of peroxidase-labeled anti-human IgG or anti-mouse IgG antibody was charged in each well and further incubated at room temperature for one hour. After washing, 100 μl of a 0.3 mM TMBZ solution containing 0.005% hydrogen peroxide was added to each well and incubated at room temperature for 10 minutes. The reaction was then terminated with the addition of 100 μl of 2N sulfuric acid. The absorbance was measured at 450 nm.

As shown in FIG. 4, the results reveal that the immobilized β2-GPI and the β2-GPI-oxidized LDL complex react competitively with aCL antibody, indicating that the oxidized LDL can be assayed using the competitive reaction.

Figure 5A:
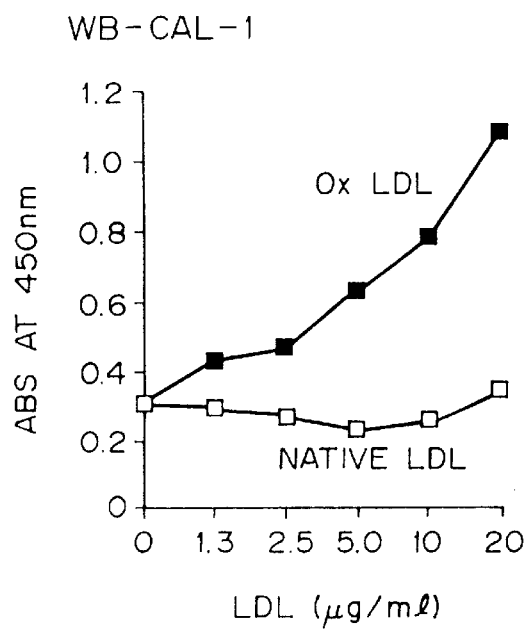
FIG. 5 shows the results of assay for an oxidized LDL by sandwich ELISA, using an aCL antibody and an anti-LDL antibody.
Figure 5B:
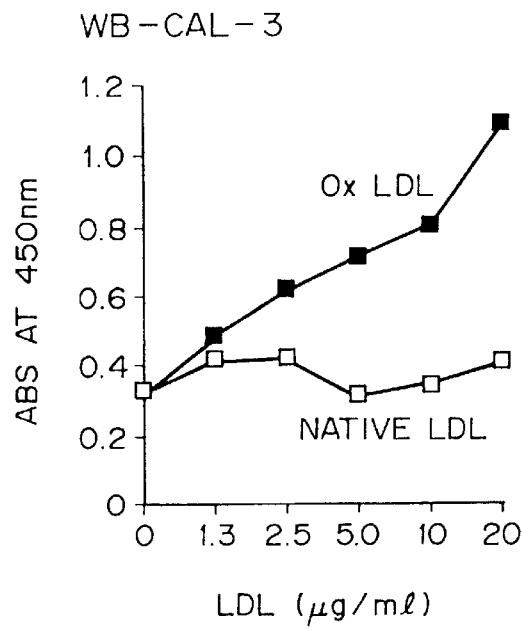

EXAMPLE 5
Assay (1) for oxidized LDL by sandwich ELISA (FIG. 5)

After 50 μl of 5 μg/ml aCL antibody (Antibody WB-CAL-1 or WB-CAL-3) was charged in each well on a polystyrene plate, the wells were incubated at 4° C. for 16 to 24 hours, then washed with PBS-Tween. Thereafter 50 μl of a solution containing appropriately diluted oxidized LDL or non-oxidized LDL was added to each well, and 50 μl of 200 μg/ml β2-GPI was further added thereto followed by incubation at room temperature for an hour. After washing, 100 μl of peroxidase-labeled anti-LDL antibody (Antibody 9F5-3) was charged in each well, and incubated at room temperature for a minute. After washing, 100 μl of a 0.3 mM TMBZ solution containing 0.005% hydrogen peroxide was added to each well, and incubated at room temperature for 10 minutes. The reaction was then terminated with the addition of 100 μl of 2N sulfuric acid. The absorbance was measured at 450 nm.

As shown in FIG. 5, the results reveal that the β2-GPI-oxidized LDL complex can be specifically assayed by the sandwich method using the aCL antibody and anti-LDL antibody, indicating that the method can be used in an assay for oxidized LDL.

Figure 6A:
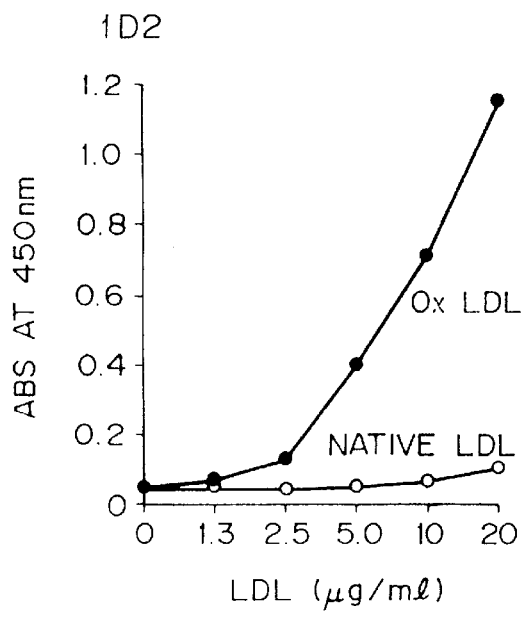
FIG. 6 shows the results of assay for an oxidized LDL by sandwich ELISA, using an anti-apo B protein antibody and an anti-β2-GPI antibody.
Figure 6B:
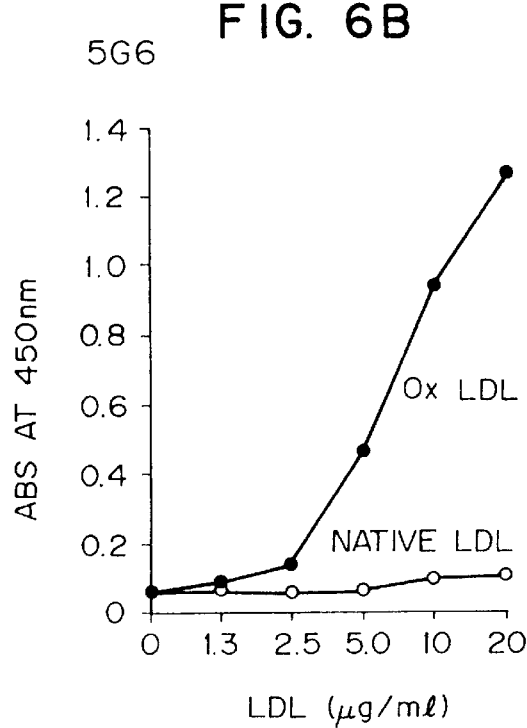

EXAMPLE 6
Assay (2) for oxidized LDL by sandwich ELISA (FIG. 6)

After 50 μl of 5 μg/ml anti-apo B protein antibody (Antibody 1D2 or 5G6) was charged in each well on a polystyrene plate, the wells were incubated at 4° C. for 16 to 24 hours, then washed three times with PBS-Tween. Thereafter 50 μl of a sample containing appropriately diluted oxidized LDL or non-oxidized LDL was added to each well, and 50 μl of 200 μg/ml β2-GPI was further added thereto followed by incubation at room temperature for an hour. After washing, 100 μl of peroxidase-labeled anti-β2-GPI antibody (Antibody Cof-22) was charged in each well, and incubated at room temperature for an hour. After washing, 100 μl of a 0.3 mM TMBZ solution containing 0.005% hydrogen peroxide was added to each well, and incubated at room temperature for 10 minutes. The reaction was then terminated with the addition of 100 μl of 2N sulfuric acid. The absorbance was measured at 450 nm.

As shown in FIG. 6, the results reveal that the β2-GPI-oxidized LDL complex can be specifically assayed by the sandwich method, using the anti-apo B protein antibody and anti-β2-GPI antibody, indicating that the method can be used in an assay for oxidized LDL.

Figure 7:
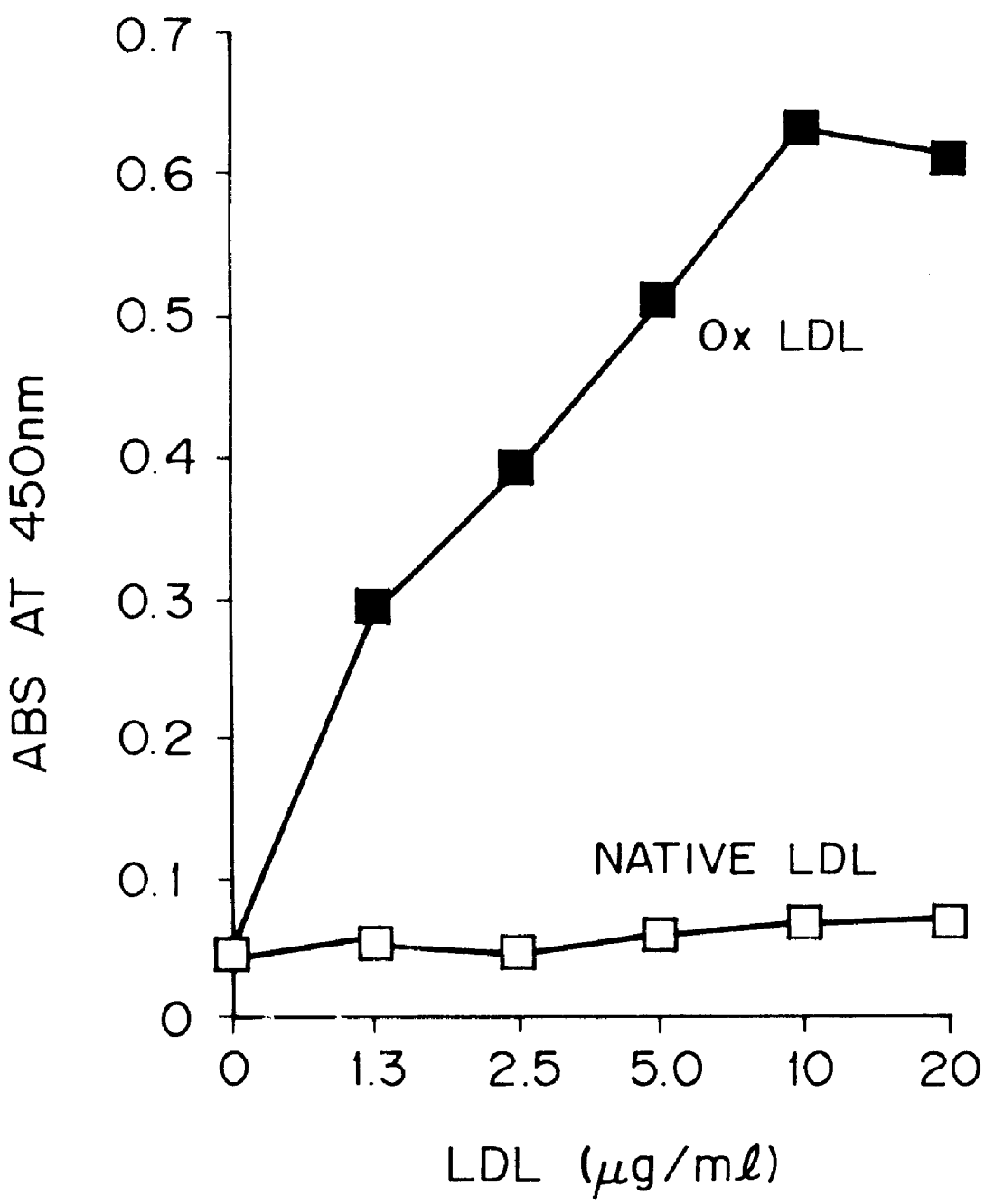
FIG. 7 shows the results of assay for an oxidized LDL by sandwich ELISA, using an anti-β2-GPI antibody and an anti-LDL antibody.

EXAMPLE 7
Assay (3) for oxidized LDL by sandwich ELISA (FIG. 7)

After 50 μl of 10 μg/ml anti-β2-GPI antibody (Antibody Cof-22) was charged in each well on a polyvinyl chloride 4° C. wells were incubated at 4° C. for 16 to 24 hours, then washed with PBS. After 200 μl of 3% gelatin solution was added to each well, the wells were incubated for an hour at room temperature. After the gelatin solution was removed, 50 μl of 100 μg/ml β2-GPI was added and incubated at room temperature for an hour. After washing, 50 μl of the oxidized LDL or non-oxidized LDL was added and incubated at room temperature for an hour. After washing, 50 μl each of peroxidase-labeled anti-LDL antibody (Antibody 10E3-3) was added to each well, and incubated at room temperature for an hour. After washing, 100 μl of a 0.3 mM TMBZ solution containing 0.005% hydrogen peroxide was added to each well, and incubated at room temperature for 10 minutes. The reaction was then terminated with the addition of 50 μl of 2N sulfuric acid. The absorbance was measured at 450 nm.

As shown in FIG. 7, the results reveal that the β2-GPI-oxidized LDL complex can be specifically assayed by the sandwich method, using anti-β2-GPI antibody and anti-LDL antibody, indicating that the method can be used in an assay for oxidized LDL.

Figure 8:
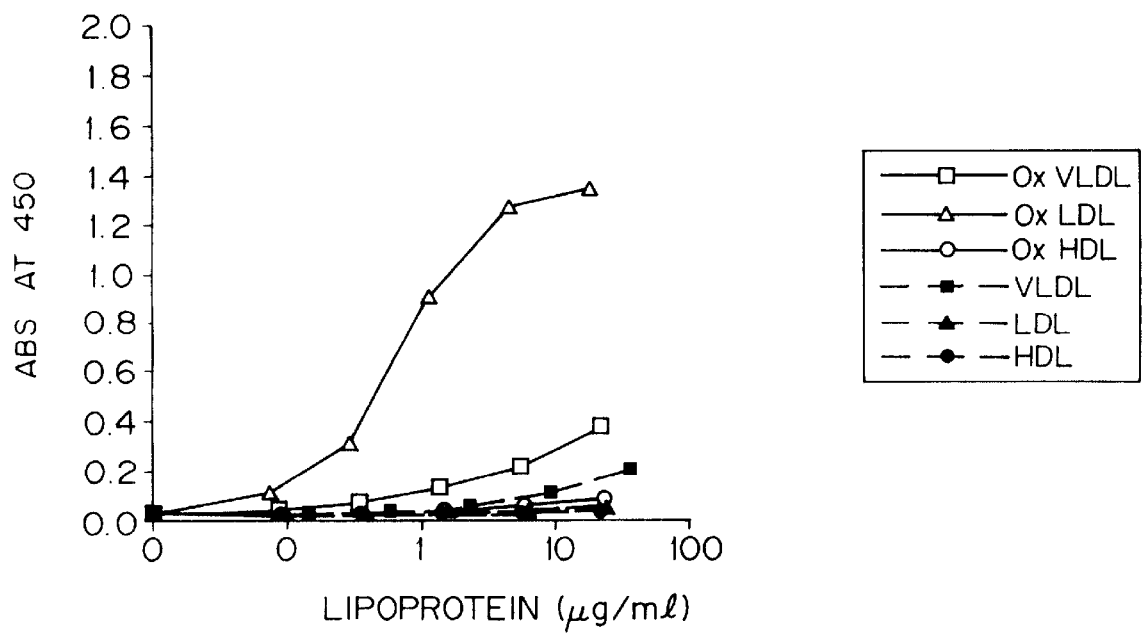
FIG. 8 shows the results of assay for an oxidized LDL by sandwich ELISA, using an anti-aCL antibody and an anti-apo B protein antibody.

EXAMPLE 8
Assay (4) for oxidized LDL by sandwich ELISA (FIG. 8)

After 50 μl of 5 μg/ml aCL antibody (Antibody WB-CAL-1) was charged in each well on a polystyrene plate, the wells were incubated at 4° C. for 16 to 24 hours, then washed with PBS. After 300 μl of 3% gelatin solution was added to each well, the wells were incubated for an hour at room temperature. After the gelatin solution was removed, 50 μl of 200 μg/ml β2-GPI and further 50 μl of appropriately diluted lipoprotein were added thereto followed by incubation at room temperature for 2 hours. After washing with PBS, 50 μl of peroxidase-labeled anti-apo B protein antibody (Antibody 1D2) was added to each well, and incubated at room temperature for an hour. After washing with PBS, 100 μl of a 0.3 mM TMBZ solution containing 0.005% hydrogen peroxide was added to each well, and incubated at room temperature for 20 minutes. The reaction was then terminated with the addition of 50 μl of 2N sulfuric acid. The absorbance was measured at 450 nm.

As shown in FIG. 8, the results reveal that the β2-GPI-oxidized LDL complex can be specifically assayed by the sandwich method using the aCL antibody and anti-apo B protein antibody, indicating that the method can be used in an assay for oxidized LDL.

Figure 9:
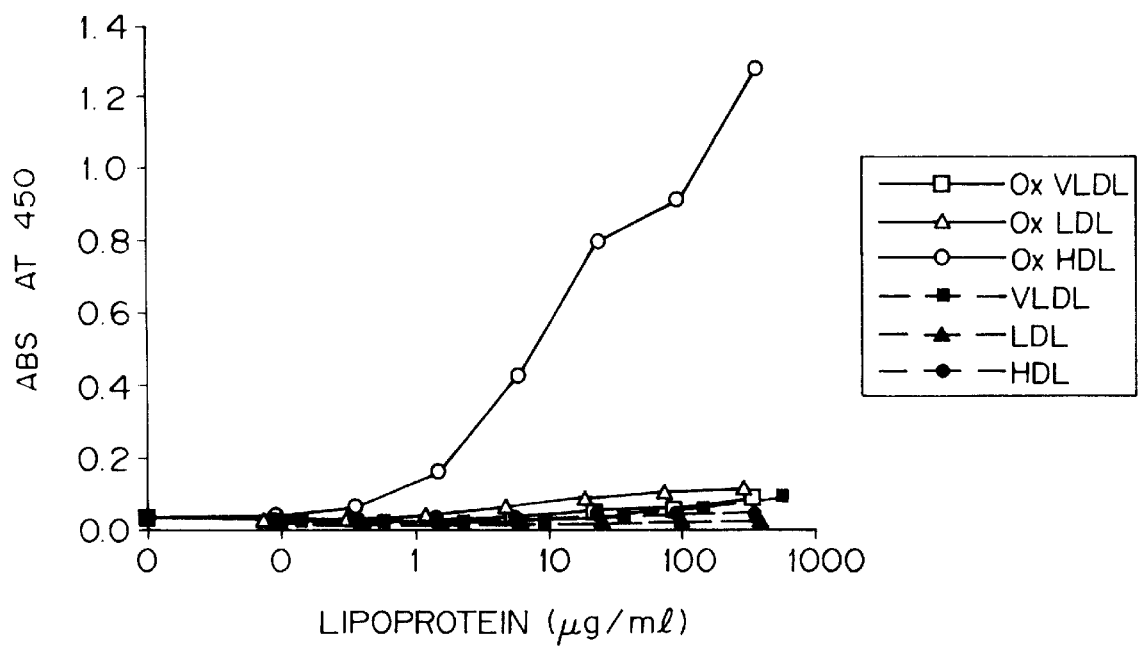
FIG. 9 shows the results of assay for an oxidized HDL by sandwich ELISA, using an anti-aCL antibody and an anti-HDL antibody.

EXAMPLE 9
Assay for oxidized HDL by sandwich ELISA (FIG. 9)

After 50 μl of 5 μg/ml aCL antibody (Antibody WB-CAL-1) was charged in each well on a polystyrene plate, the wells were incubated at 4° C. for 16 to 24 hours, then washed with PBS. After 300 μl of 3% gelatin solution was added to each well, the wells were incubated for an hour at room temperature. After the gelatin solution was removed, 50 μl of 200 μg/ml β2-GPI and further 50 μl of appropriately diluted lipoprotein were added thereto followed by incubation at room temperature for 2 hours. After washing with PBS, 50 μl of peroxidase-labeled anti-HDL antibody (H1) was added to each well, and incubated at room temperature for an hour. After washing with PBS, 100 μl of a 0.3 mM TMBZ solution containing 0.005% hydrogen peroxide was added to each well, and incubated at room temperature for 20 minutes. The reaction was then terminated with the addition of 50 μl each of 2N sulfuric acid. The absorbance was measured at 450 nm.

As shown in FIG. 9, the results reveal that the β2-GPI-oxidized HDL complex can be specifically assayed by the sandwich method using the aCL antibody and anti-HDL antibody, indicating that the method can be used in an assay for oxidized HDL.

Figure 10:
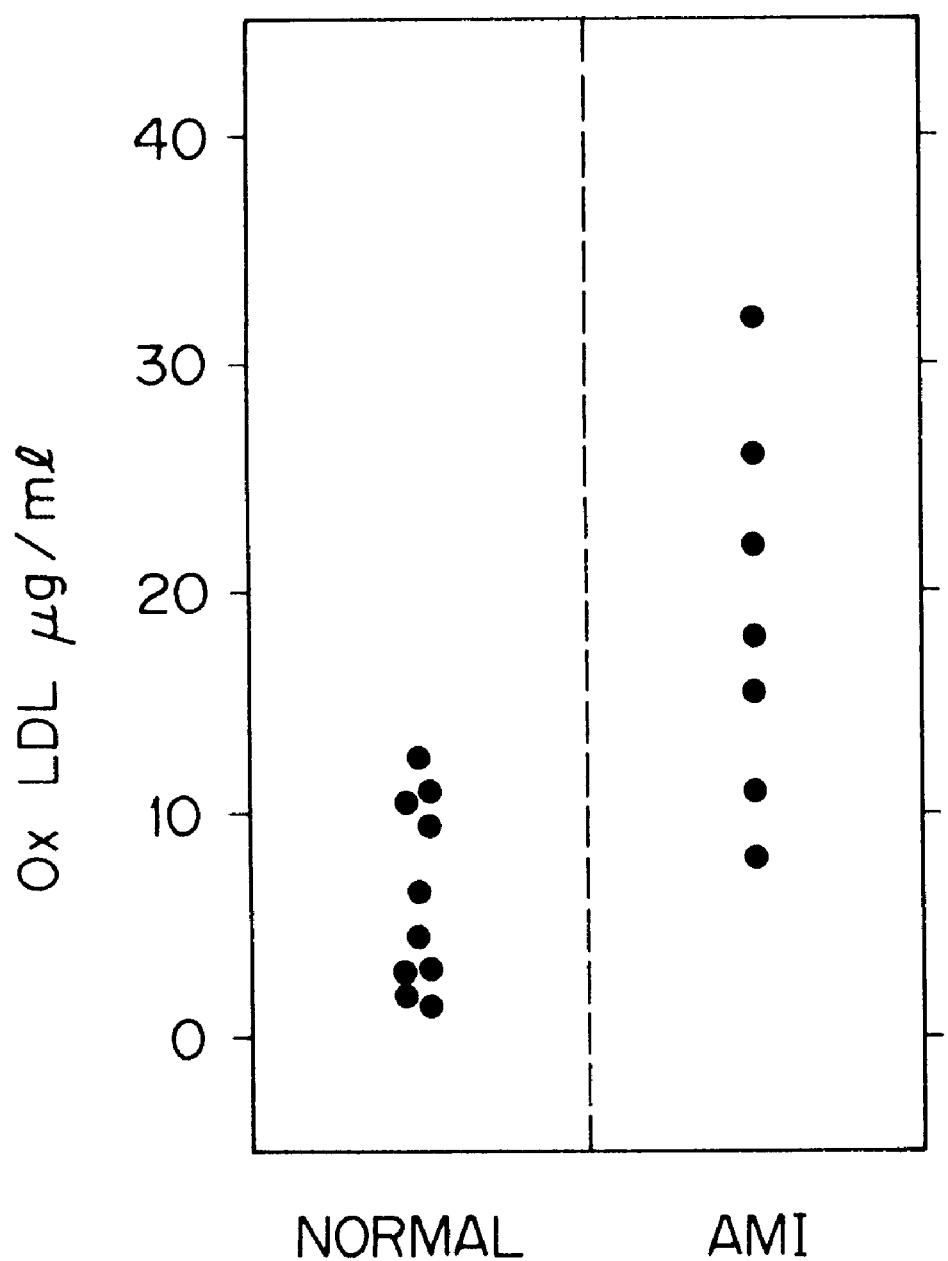
FIG. 10 shows the results of quantative assay for an oxidized LDL present in blood from normal persons and patients with acute myocardial infarction.

EXAMPLE 10
Assay for oxidized LDL in serum (FIG. 10)

After 50 μl of 5 μg/ml aCL antibody (Antibody WB-CAL-1) was charged in each well on a polystyrene plate, the wells were incubated at 4° C. for 16 to 24 hours, then washed with PBS. After 300 μl of 3% gelatin solution was added to each well, the wells were allowed to stand for an hour at room temperature for blocking. After the gelatin solution was removed, 50 μl of 200 μg/ml β2-GPI and further 50 μl of a sample containing appropriately diluted serum were added thereto followed by incubation at room temperature for 2 hours. After washing with PBS, 100 μl of peroxidase-labeled anti-apo B protein antibody (Antibody 1D2) was added to each well, and incubated at room temperature for an hour. After washing with PBS, 100 μl of a 0.3 mM TMBZ solution containing 0.005% hydrogen peroxide was added to each well, and incubated at room temperature for 20 minutes. The reaction was then terminated with the addition of 50 μl of 2N sulfuric acid. The absorbance was measured at 450 nm.

As shown in FIG. 10, the results reveal that the oxidized LDL present in the sample from the patient with acute myocardial infarction showed a significantly high level, as compared to that of the normal serum sample.

Industrial Applicability

The assay method and kit for use in the method of the present invention utilize the specific binding of an oxidized lipoprotein to β2-GPI. The present invention can provide a practical method for determination of a lipoprotein, utilizing the specific binding of an oxidized lipoprotein to B2-GPI.

According to the present invention, an oxidized lipoprotein in a sample is assayed as the β2-GPI-oxidized lipoprotein complex which is originally present in blood. Therefore, the assay data obtained in the present invention reflect well the clinical conditions of arteriosclerotic disease (for example, diabetic arteriosclerosis, myocardial infarction, cerebral infarction, and the like). The present invention is thus useful for diagnosis (screening) of these diseases.

We claim:

1. A method for detecting the presence or absence of an oxidized lipoprotein in a sample comprising:
    providing a sample containing β2-glycoprotein I ("β2-GPI") wherein the β2-GPI forms a complex of β2-GPI and oxidized lipoprotein, if the oxidized lipoprotein is present in the sample,
    assaying by a sandwich assay method for the complex of β2-GPI and oxidized lipoprotein in the sample by reacting the sample with at least two antibody reagents comprising at least one solid phase antibody reagent selected from the group consisting of (1) an anti-cardiolipin antibody immobilized on a carrier, (2) an anti-lipoprotein antibody immobilized on a carrier, (3) an anti-apolipoprotein antibody immobilized on a carrier and (4) an anti-β2-GPI antibody immobilized on a carrier, and at least one labeled soluble phase antibody reagent selected from the group consisting of (1) an anti-cardiolipin antibody, (2) an anti-lipoprotein antibody (3) an anti-apolipoprotein antibody and (4) an anti-β2-GPI antibody, and
    detecting the presence or absence of the complex bound to the labeled soluble phase antibody reagent wherein the complex is indicative of the presence of the oxidized lipoprotein in the sample.

2. The method according to claim 1, wherein the solid phase antibody reagent is the anti-cardiolipin antibody immobilized on a carrier, and the soluble phase antibody reagent is the anti-lipoprotein antibody, the anti-apolipoprotein antibody, or the anti-β2-GPI antibody.

3. The method according to claim 1, wherein the solid phase antibody reagent is the anti-cardiolipin antibody immobilized on a carrier, and the soluble phase antibody reagent is the anti-lipoprotein antibody or the anti-apolipoprotein antibody, and the anti-β2-GPI antibody.

4. The method according to claim 1, wherein the solid phase antibody reagent is the anti-lipoprotein antibody immobilized on a carrier or the anti-apolipoprotein antibody immobilized on a carrier, and the soluble phase antibody reagent is the anti-cardiolipin antibody or the anti-β2-GPI antibody.

5. The method according to claim 1, wherein the solid phase antibody reagent is the anti-lipoprotein antibody immobilized on a carrier or the anti-apolipoprotein antibody immobilized on a carrier, and the soluble phase antibody reagent is the anti-cardiolipin antibody and the anti-β2-GPI antibody.

6. The method according to claim 1, wherein the solid phase antibody reagent is the anti-β2-GPI antibody immobilized on a carrier, and the soluble phase antibody reagent is the anti-cardiolipin antibody, the anti-lipoprotein antibody or the anti-apolipoprotein antibody.

7. The method according to claim 1, wherein the solid phase antibody reagent is the anti-β2-GPI antibody immobilized on a carrier, and the soluble phase antibody reagent is the anti-lipoprotein antibody or the anti-apolipoprotein antibody, and the anti-cardiolipin antibody.

8. The method according to claim 1, wherein the solid phase antibody reagent is the anti-cardiolipin antibody immobilized on a carrier, and the soluble phase antibody reagent is the anti-cardiolipin antibody.

9. A method for assessing quantitatively the presence or absence of an oxidized lipoprotein in a sample comprising:

providing a sample containing β2-GPI wherein the β2-GPI forms a complex of β2-GPI and oxidized lipoprotein, if the oxidized lipoprotein is present in the sample, assaying by a sandwich assay method for the complex of β2-GPI and oxidized lipoprotein in the sample by reacting the sample with at least two antibody reagents comprising at least one solid phase antibody reagent selected from the group consisting of (1) an anti-cardiolipin antibody immobilized on a carrier, (2) an anti-lipoprotein antibody immobilized on a carrier, (3) an anti-apolipoprotein antibody immobilized on a carrier and (4) an anti-β2-GPI antibody immobilized on a carrier, and at least one labeled soluble phase antibody reagent selected from the group consisting of (1) an anti-cardiolipin antibody, (2) an anti-lipoprotein antibody (3) an anti-apolipoprotein antibody and (4) an anti-β2-GPI antibody, and assessing quantitatively the presence or absence of the complex bound to the labeled soluble phase antibody reagent wherein the complex is indicative of the quantity of the oxidized lipoprotein in the sample.

10. The method according to claim 9, wherein the assessment is indicative of a risk for an arteriosclerotic disease.

* * * * *